(12) United States Patent
Healy et al.

(10) Patent No.: US 6,949,249 B2
(45) Date of Patent: Sep. 27, 2005

(54) SKIN PROTECTANT SPRAY COMPOSITIONS

(75) Inventors: Michael Sean Healy, Denville, NJ (US); Dennis George Anthony Nelson, Mountain Lakes, NJ (US)

(73) Assignee: Pfizer Inc., Morris Plains, NJ (US)

( * ) Notice: Subject to any disclaimer, the term of this patent is extended or adjusted under 35 U.S.C. 154(b) by 168 days.

(21) Appl. No.: 10/275,994

(22) PCT Filed: Apr. 30, 2001

(86) PCT No.: PCT/IB01/00717

§ 371 (c)(1),
(2), (4) Date: Nov. 7, 2002

(87) PCT Pub. No.: WO01/85128

PCT Pub. Date: Nov. 15, 2001

(65) Prior Publication Data

US 2003/0082223 A1 May 1, 2003

Related U.S. Application Data

(60) Provisional application No. 60/202,467, filed on May 8, 2000.

(51) Int. Cl.⁷ .......................... A61K 7/00; A61K 31/74; A61K 33/32; A61K 9/00
(52) U.S. Cl. ...................... 424/401; 424/47; 424/78.03; 424/78.05; 424/78.06; 424/400; 424/642; 514/865
(58) Field of Search ................................. 424/400, 401, 424/47, 642, 78.03, 78.05, 78.06; 514/865

(56) References Cited

U.S. PATENT DOCUMENTS

| | | |
|---|---|---|
| 3,770,648 A | 11/1973 | Mackles |
| 4,382,919 A | 5/1983 | Alonso et al. |
| 4,446,131 A | 5/1984 | Maughan |
| 4,594,332 A | 6/1986 | Hoelderich et al. |
| 4,672,074 A | 6/1987 | Harendza-Harinxma |
| 4,725,438 A | 2/1988 | Leazer |
| 4,760,095 A | 7/1988 | Djerassi et al. |
| 4,847,071 A | 7/1989 | Bissett et al. |
| 4,911,932 A | 3/1990 | Clum et al. |
| 4,917,890 A | 4/1990 | McAnalley |
| 4,938,960 A | 7/1990 | Ismail |
| 4,971,800 A | 11/1990 | Chess et al. |
| 4,996,238 A | 2/1991 | Matravers |
| 4,996,239 A | 2/1991 | Matravers |
| 5,045,317 A | 9/1991 | Chess et al. |
| 5,051,260 A | 9/1991 | Chess et al. |
| 5,091,193 A | 2/1992 | Enjolras et al. |
| 5,093,107 A | 3/1992 | Matravers |
| 5,232,691 A | 8/1993 | Lemole |
| 5,234,689 A | 8/1993 | Lindauer et al. |
| 5,266,318 A | 11/1993 | Taylor-McCord |
| 5,292,530 A * | 3/1994 | McCrea et al. ............... 424/66 |
| 5,384,115 A | 1/1995 | Bissett et al. |
| 5,427,776 A | 6/1995 | Isnard |
| 5,436,007 A | 7/1995 | Hartung et al. |
| 5,444,096 A | 8/1995 | McCrea et al. |
| 5,468,737 A | 11/1995 | McAnalley et al. |
| 5,541,220 A | 7/1996 | Ismail |
| 5,602,183 A | 2/1997 | Martin et al. |
| 5,635,189 A | 6/1997 | Horrobin et al. |
| 5,652,261 A | 7/1997 | Ismail |
| 5,679,359 A | 10/1997 | Diezel |
| 5,695,771 A | 12/1997 | Boussouira et al. |
| 5,747,010 A | 5/1998 | Geesin et al. |
| 5,786,384 A | 7/1998 | Ismail |
| 5,824,323 A | 10/1998 | Fishman |
| 5,882,657 A | 3/1999 | Miguel-Colombel et al. |
| 5,914,101 A | 6/1999 | Tapley et al. |
| 5,938,649 A | 8/1999 | Ducker et al. |
| 5,939,053 A | 8/1999 | Forestier et al. |
| 5,939,395 A | 8/1999 | Yu et al. |
| 5,944,705 A | 8/1999 | Ducker et al. |
| 5,961,961 A | 10/1999 | Dobkowski et al. |
| 5,965,137 A | 10/1999 | Petrus |
| 5,972,359 A | 10/1999 | Sine et al. |
| 5,976,517 A | 11/1999 | Dubief et al. |
| 6,001,377 A | 12/1999 | SaNogueira, Jr. et al. |
| 6,007,800 A | 12/1999 | Dubief et al. |
| 6,011,126 A | 1/2000 | Dubief et al. |
| 6,103,245 A * | 8/2000 | Clark et al. ................. 424/401 |
| 6,103,247 A | 8/2000 | Boussouira et al. |
| 6,103,644 A | 8/2000 | Sheridan |
| 6,149,934 A | 11/2000 | Krzysik et al. |
| 6,235,293 B1 | 5/2001 | De La Poterie et al. |
| 6,254,876 B1 | 7/2001 | De la Poterie et al. |
| 6,254,877 B1 | 7/2001 | De La Poterie et al. |
| 6,261,574 B1 | 7/2001 | Costello |
| 6,383,502 B1 * | 5/2002 | Dunshee et al. ............ 424/401 |
| 6,627,178 B1 | 9/2003 | Cawthon |
| 2001/0006665 A1 | 7/2001 | Auguste |
| 2001/0006671 A1 | 7/2001 | Goodman et al. |
| 2001/0016604 A1 | 8/2001 | Yu et al. |
| 2001/0031269 A1 | 10/2001 | Arnaud |
| 2001/0051171 A1 | 12/2001 | Mondet |

FOREIGN PATENT DOCUMENTS

| | | |
|---|---|---|
| EP | 359488 A2 * | 3/1990 |
| JP | 24126 87 | 2/1987 |
| JP | 24962092 | 9/1992 |
| JP | 21434194 | 8/1994 |
| WO | WO9926597 | 6/1999 |
| WO | 9959540 | 11/1999 |
| WO | WO0001362 | 1/2000 |

* cited by examiner

Primary Examiner—Gary Kunz
Assistant Examiner—Marina Lamm
(74) Attorney, Agent, or Firm—Barry H. Jacobsen; Evan J. Federman

(57) ABSTRACT

A liquid, water-repellent, substantially anhydrous, spray-pumpable skin protectant composition is disclosed. The composition is designed for spraying directly onto skin, has suitable adherence to the skin, and resists running. The composition contains one or more actives, one or more rheology modifiers, and a carrier. The rheological modifiers can be waxes and/or associative thickeners such as some forms of silica. The carrier can be mineral oil or a mineral oil replacement (e.g., isohexadecane, cyclomethicone). Film-forming components also help the composition resist running. One indication for which the composition may be formulated is diaper rash. The active ingredient for diaper rash may be dimethicone and preferably also zinc oxide.

7 Claims, No Drawings

SKIN PROTECTANT SPRAY COMPOSITIONS

This application claims the benefit of International Application PCT/IB01/00717, filed Apr. 30, 2001, which claims priority to U.S. Provisional Patent Application No. 60/202,467, filed May 8, 2000.

BACKGROUND OF THE INVENTION

1. Technical Field

This invention concerns topical formulations and, more particularly, topical skin protectant formulations that can be sprayed.

2. Background

Drugs and other substances are often applied to human skin to protect it from harmful stimuli. The U.S. Food And Drug Administration ("FDA") has in the past defined a "skin protectant" as a drug that protects injured or exposed skin or mucous membrane surfaces from harmful or annoying stimuli (21 CFR §347.3 (1983)). Thus, a "skin protectant" can be used to protect and/or treat skin in connection with various indications, including diaper rash; minor burns; cuts; scrapes; sunburn; chaffed, chapped, cracked, or windburned skin or lips; skin irritation; and oozing and/or weeping of skin caused by poison ivy, poison oak, and/or poison sumac.

The skin of infants is known to be highly sensitive, particularly to chemical substances. One common skin problem of infants is diaper dermatitis, more commonly called "diaper rash." "Diaper rash" has been defined by the FDA as an inflammatory skin condition in the diaper area (perineum, buttocks, lower abdomen, and inner thighs) caused by one or more of the following factors: moisture, occlusion, chaffing, continued contact with urine or feces or both, or mechanical or chemical irritation (21 CFR §347.3 (1990)), and that definition will be used herein. The FDA has also indicated that mild diaper rash appears as simple erythema and that more severe conditions may be accompanied by papules, vesicles, oozing, and ulceration. Adults (e.g., incontinent adults) may also suffer from diaper rash.

Strategies for dealing with diaper rash include removing the source of irritation, reducing the immediate skin reaction, relieving discomfort, and preventing secondary infection. Many products used in treating diaper rash are designed to provide a barrier between the skin and the waste products. Known barrier ingredients include zinc oxide and petrolatum. Barrier products containing oily substances such as petrolatum may feel greasy, may be difficult to apply because of their high viscosity, and may not be easily removed from hands that apply the products or from the infant's skin. Clean-up of these products from the hands and from the infant's skin may be regarded by some as time-consuming, messy, and inconvenient.

The FDA will allow claims to be made that the following substances are useful as skin protectants provided, among other things, that those substances are used at FDA-specified concentration levels: mineral oil, dimethicone, zinc oxide, allantoin, calamine, kaolin, petrolatum, white petrolatum, cod liver oil, lanolin, talc, topical starch, aluminum hydroxide gel, cocoa butter, glycerine, shark liver oil, zinc acetate, and zinc carbonate, all of which will be referred to herein as "active ingredients for protecting skin" (21 CFR §347.10 (1983 and 1990)). As used herein, the terms "protecting skin," "protecting the skin," and "protecting human skin" are synonymous and each include protecting and/or treating skin in connection with various indications involving the skin, including diaper rash; minor burns; cuts; scrapes; sunburn; chaffed, chapped, cracked, or windburned skin or lips; skin irritation; and oozing and/or weeping of skin caused by poison ivy, poison oak, and/or poison sumac.

The FDA will allow claims to be made that the following substances are useful in treating diaper rash provided, among other things, that those substances are used at FDA-specified concentration levels: mineral oil, dimethicone, zinc oxide, allantoin, calamine, kaolin, petrolatum, white petrolatum, cod liver oil, lanolin, talc, and topical starch, all of which will be referred to herein as "active ingredients for treating diaper rash" (21 CFR §347.10 (1983 and 1990)). For example, assuming all the other requirements are met, the FDA will allow a claim to be made that a composition containing dimethicone is useful for treating diaper rash if the dimethicone concentration is from 1% w (percent by weight) to 30% w. A similar claim can be made for a composition containing zinc oxide if the zinc oxide concentration is from 1% w to 40% w. A similar claim can be made for a composition containing mineral oil if the mineral oil concentration is from 50% w to 100% w. As used herein, the term "treating diaper rash" includes treating an existing diaper rash condition or preventing a diaper rash condition or both.

Compositions that may contact the skin and may contain zinc oxide, and/or mineral oil, and/or silicon dioxide (silica), and/or dimethicone or other silicone compounds, some of which compositions may be in the form of aerosols or sprays and some of which compositions may be used for treating diaper rash, include those compositions referred to in U.S. Pat. Nos. Re. 33,107, 2,843,522, 3,770,648, 3,935,862, 4,043,077, 4,196,218, 4,273,786, 4,278,658, 4,329,366, 4,389,418, 4,514,383, 4,556,560, 4,569,839, 4,574,082, 4,672,074, 4,725,438, 4,800,076, 4,816,254, 4,842,593, 4,847,071, 4,911,932, 4,933,330, 4,938,960, 4,996,238, 4,996,239, 5,043,359, 5,085,856, 5,137,714, 5,208,031, 5,210,102, 5,232,691, 5,234,689, 5,266,318, 5,362,488, 5,389,204, 5,436,007, 5,527,519, 5,543,135, 5,545,673, 5,558,872, 5,573,753, 5,576,006, 5,603,863, 5,616,331, 5,635,191, 5,643,588, 5,652,274, 5,662,937, 5,665,426, 5,730,993, 5,733,895, 5,744,146, 5,756,082, 5,756,110, 5,762,945, 5,776,440, 5,834,290, 5,861,143, 5,861,144, 5,861,146, 5,863,522, 5,869,061, 5,869,062, 5,869,071, 5,874,094, 5,885,599, 5,914,101, 5,939,053, 5,945,211, 5,958,397, 5,961,961, 5,962,441, 5,965,137, 5,965,610, 5,968,531, and 5,972,359. (All of the these documents and any other documents discussed or otherwise referenced or identified herein are incorporated herein in their entireties for all purposes.)

Compositions containing zinc oxide that may contact the skin include those referred to in U.S. Pat. Nos. 2,843,522, 3,770,648, 4,034,077, 4,278,658, 4,389,418, 4,556,560, 4,569,839, 4,672,074, 4,816,254, 4,911,932, 4,933,330, 5,085,856, 5,208,031, 5,232,691, 5,527,519, 5,543,135, 5,545,673, 5,573,753, 5,603,863, 5,616,331, 5,652,274, 5,662,937, 5,665,426, 5,730,993, 5,733,895, 5,744,146, 5,756,110, 5,762,945, 5,834,290, 5,861,143, 5,861,144, 5,861,146, 5,863,522, 5,869,062, 5,874,094, 5,885,599, 5,914,101, 5,939,053, 5,945,211, 5,961,961, 5,962,441, 5,965,610, 5,968,531, and 5,972,359.

Some of the compositions containing zinc oxide may be sprayable (with or without a propellant). See, e.g., U.S. Pat. Nos. 3,770,648, 4,278,658, 4,933,330, 5,652,274, 5,733,895, 5,834,290, 5,861,143, 5,861,144, 5,861,146, 5,863,522, 5,885,599, 5,939,053, 5,945,211, 5,962,441, 5,965,610, and 5,972,359.

Some of the compositions containing zinc oxide may contain small zinc oxide particles (e.g., less than 1 micron).

See, e.g., U.S. Pat. Nos. 5,543,135, 5,527,519, 5,573,753, 5,603,863, 5,616,331, 5,730,993, 5,756,110, 5,861,143, 5,861,144, 5,861,146, 5,914,101, 5,945,211, 5,961,961, and 5,972,359.

Topical compositions for treating diaper rash containing zinc oxide include DESITIN® Ointment and DESITIN® Creamy Ointment, both marketed by Pfizer Inc, the assignee of the present application. DESITIN® Ointment contains about 40% w zinc oxide and other ingredients, including white petrolatum, cod liver oil, lanolin, talc, and about 5% w water. DESITIN® Creamy Ointment contains about 10% w zinc oxide and other ingredients, including mineral oil, mineral wax, dimethicone, cyclomethicone, white petrolatum, white wax, and over 30% w water.

Other diaper rash, incontinence/dermatitis, diaper-treating, and baby treatment compositions include those referred to in U.S. Pat. Nos. Re.33,107, 2,843,522, 3,770,648, 3,935,862, 4,034,077, 4,273,786, 4,329,366, 4,556,560, 4,816,254, 4,842,593, 4,911,932, 4,996,238, 4,996,239, 5,362,488, 5,436,007, 5,576,006, 5,558,872, 5,635,191, 5,643,588, 5,652,274, 5,762,945, 5,834,290, 5,869,071, and 5,945,211.

Some of those diaper rash, incontinence/dermatitis, diaper-treating, and baby treatment compositions may form a film when they are topically applied and may be resistant to wetting by moisture. See, e.g., U.S. Pat. No. 4,996,238 (column 2, line 20 and following) and U.S. Pat No. 4,996,239(column 2, line 40 and following).

Some of those diaper rash, incontinence/dermatitis, diaper-treating, and baby treatment compositions may contain film-forming agents. See, e.g., U.S. Pat. No. 4,996,238 (column 2, line 42 and following), U.S. Pat. No. 4,996,239 (column 2, line 63 and following), U.S. Pat. No. 5,635,191 (column 18, line 34), and U.S. Pat. No. 5,643,588 (column 18, line 47).

Some of those diaper rash, incontinence/dermatitis, diaper-treating, and baby treatment compositions may be sprayable (with or without a propellant). See, e.g., U.S. Pat. Nos. Re.33,107, 3,770,648, 3,935,862, 4,273,786, 4,329,366, 4,842,593, 5,436,007, 5,576,006, 5,635,191, 5,643,588, 5,652,274, 5,869,071, and 5,945,211.

U.S. Pat. No. Re. 33,107 refers to sprays that may contain mineral oil for treating skin conditions such as dermatitis.

U.S. Pat. No. 3,770,648, assigned on its face to Bristol-Myers Company, refers to substantially non-aqueous quick-breaking aerosol foaming compositions containing silicone compounds (e.g., dimethyl silicone fluids), foamable organic liquids (e.g., mineral oil), and a high vapor pressure propellant system (e.g., fluorocarbons). Example 2 of the patent refers to what is called "DESITIN® baby foam," containing zinc oxide (about 4.2% w), mineral oil (about 71.7% w), a silicone, and FREON 12 fluorocarbon propellant.

U.S. Pat. Nos. 3,935,862 and 4,273,786 refer to compositions containing amino acid compounds to inhibit the formation of ammonia and therefore treat diaper rash. The compositions may contain solid diluents such as starch and talc and may also contain silicone-type fluids such as polysiloxane fluid. Although mineral oil is referred to in some of the non-sprayable compositions exemplified in the patents, the only sprayable composition (Example H) contains micropulverized talc, an amino acid salt, fragrance, anhydrous ethanol, isopropyl myristate, and two FREON propellants.

U.S. Pat. No. 4,329,366 refers to compositions containing acylaminophenols that can be used to treat various conditions, including diaper rash. Although mineral oil is referred to in some of the non-sprayable formulations exemplified, the two sprayable formulations (Formulations F and L) use alcohol and propellants and at least one of them (Formulation F) contains water.

U.S. Pat. No. 4,842,593 refers to a pH control system that can be sprayed onto an article used to prevent or reduce diaper rash. The fibers of the article may be impregnated with silica.

U.S. Pat. No. 5,436,007 refers to a diaper rash lotion that may be sprayed containing dimethicone (e.g., from 1% w to 30% w), water (e.g., from 50% w to 95% w), and an emulsifier (e.g., from 1% w to 10% w). The patent also refers to a diaper rash cream that may contain a linear polydimethylsiloxane (e.g., 20% w), a light mineral oil (e.g., 4% w), emulsifier (e.g., 8% w), and water (e.g., over 40% w). Stearic acid, which is said to function as a thickener, and aloe may also be used in the lotion and the cream. See, e.g., column 7, line 6, to column 10, line 26.

U.S. Pat. No. 5,576,006 refers to antibacterial compositions that can be used to deodorize footwear and to treat diaper rash. Although the footwear deodorizing compositions can be sprays, it appears that the compositions intended for use on infants are "body preparations and powders," which may contain talc (column 3, lines 47–63, and Example 3). The sprays exemplified contain water.

U.S. Pat. Nos. 5,635,191 and 5,643,588 refer to a diaper having a topsheet coated with a composition containing emollients (such as mineral oil, petrolatum or mineral wax, and polysiloxanes) and other ingredients (such as viscosity modifiers and film formers). The composition may be sprayed onto the topsheet. According to the patents, the composition on the diaper topsheet is transferred to the wearer's skin and those topsheets provide "BM [bowel movement] cleaning, therapeutic or protective lotion coating benefits" (U.S. Pat. No. 5,635,191, column 2, line 64, to column 3, line 52; and U.S. Pat. No. 5,643,588, column 2, line 62, to column 3, line 51). The composition is "solid" or "semisolid" at 20 degrees Centigrade (U.S. Pat. No. 5,635,191, column 9, lines 35–67; and U.S. Pat. No. 5,643,588, column 9, line 39, to column 10, line 4) and is "substantially free of water" (U.S. Pat. No. 5,635,191, column 10, lines 43–54, and U.S. Pat. No. 5,643,588, column 10, lines 48–59).

U.S. Pat. No. 5,652,274 refers to therapeutic wound healing compositions. Compositions for treating diaper dermatitis are discussed, for example, at column 11, lines 31–49; column 15, lines 39–61; column 26, lines 5–26; and column 138, line 52, to column 145, line 4. Those compositions may contain zinc oxide. At least some compositions may be sprayed (for example, the formulations of Embodiment One; see column 42, line 26). Some of the compositions may contain petrolatum, mineral oil, and vitamin E (see, e.g., column 66, lines 35–49).

U.S. Pat. No. 5,869,071 refers to a spray composition for incontinent patients that "cleanses, moisturizes and leaves a protective petrolatum barrier against wetness and irritants in one step" (column 1, lines 58–63). The composition is said to be an emulsion of water and petrolatum (or petroleum jelly) and may contain dimethicone, cyclomethicone, mineral oil, vitamin E, and aloe.

U.S. Pat. No. 5,945,211 refers to a composite to which zinc oxide particles are adhered. The composite may be a diaper and the zinc oxide may be deposited on the composite from an aqueous medium (e.g., by spraying an aqueous suspension of zinc oxide).

Sprayable (with or without a propellant) compositions that may contact the skin and that may contain dimethicone or other silicon compounds include those referred to in U.S. Pat. Nos. 3,770,648, 3,935,862, 4,273,786, 4,514,383, 4,847,071, 4,933,330, 5,137,714, 5,266,318, 5,389,204, 5,436,007, 5,635,191, 5,643,588, 5,733,895, 5,776,440, 5,834,290, 5,861,143, 5,861,144, 5,861,146, 5,863,522, 5,869,071, 5,885,599, 5,939,053, 5,962,441, 5,965,610, and 5,972,359.

Compositions containing some form of silica (silicon dioxide) include those referred to in U.S. Pat. Nos. 4,574,082, 4,800,076, 4,996,238, 4,996,239, 5,137,714, 5,208,031, 5,527,519, 5,543,135, 5,573,753, 5,603,863, 5,616,331, 5,733,895, 5,756,082, 5,756,110, 5,834,290, 5,861,143, 5,861,144, 5,861,146, 5,863,522, 5,885,599, 5,914,101, 5,939,053, 5,968,531, and 5,972,359. Some forms of silica are said to be useful as thickeners. See, e.g., U.S. Pat. Nos. 4,996,238 and 4,996,239.

Some of those compositions containing some form of silica also may contain zinc oxide. See, e.g., U.S. Pat. Nos. 5,208,031, 5,527,519, 5,543,135, 5,573,753, 5,603,863, 5,616,331, 5,733,895, 5,756,110, 5,834,290, 5,861,143, 5,861,144, 5,861,146, 5,863,522, 5,885,599, 5,914,101, 5,939,053, 5,968,531, and 5,972,359.

Some of those compositions containing silica (with or without zinc oxide) may be sprayable. See, e.g., U.S. Pat. Nos. 5,137,714, 5,733,895, 5,834,290, 5,861,143, 5,861,144, 5,861,146, 5,863,522, 5,885,599, 5,939,053, and 5,972,359.

Some sprayable compositions may contain aloe and/or a form of vitamin E. See, e.g., U.S. Pat. Nos. 4,847,071, 5,266,318, 5,436,007, 5,861,143, 5,861,144, 5,861,146, 5,869,071, 5,885,599, 5,965,137, 5,965,610, and 5,972,359. Some of the composition containing aloe and/or a form of vitamin E may be for treating diaper rash and/or incontinence/dermatitis. See, e.g., U.S. Pat. Nos. 5,436,007 and 5,869,071.

Compositions containing (a) mineral oil or petrolatum, (b) zinc oxide, and (c) dimethicone or other silicone ingredient include those referred to in U.S. Pat. Nos. 3,770,648, 4,389,418, 4,556,560, 4,569,839, 4,911,932, 4,933,330, 5,085,856, 5,208,031, 5,232,691, 5,543,135, 5,603,863, 5,616,331, 5,665,426, 5,730,993, 5,733,895, 5,744,146, 5,756,110, 5,834,290, 5,861,143, 5,861,144, 5,861,146, 5,863,522, 5,885,599, 5,914,101, 5,939,053, 5,961,961, 5,962,441, 5,965,610, and 5,972,359. Some of those compositions may be sprayable (with or without a propellant). See, e.g., U.S. Pat. Nos. 3,770,648, 4,933,330, 5,733,895, 5,834,290, 5,861,143, 5,861,144, 5,861,146, 5,863,522, 5,885,599, 5,939,053, 5,962,441, 5,965,610, and 5,972,359. Some of those compositions may be for treating diaper rash. See, e.g., U.S. Pat. Nos. 4,556,560 and 4,911,932.

Some of those compositions containing (a) mineral oil or petrolatum, (b) zinc oxide, and (c) dimethicone or other silicone ingredient may also contain silica. See, e.g., U.S. Pat. Nos. 5,208,031, 5,543,135, 5,603,863, 5,616,331, 5,733,895, 5,756,110, 5,834,290, 5,861,143, 5,861,144, 5,861,146, 5,863,522, 5,885,599, 5,914,101, 5,939,053, and 5,972,359. Some of those compositions may be sprayable (with or without a propellant). See, e.g., U.S. Pat. Nos. 5,733,895, 5,834,290, 5,861,143, 5,861,144, 5,861,146, 5,863,522, 5,885,599, 5,939,053, and 5,972,359.

Some of those compositions containing (a) mineral oil or petrolatum, (b) zinc oxide, and (c) dimethicone or other silicone ingredient may also contain wax. See, e.g., U.S. Pat. Nos. 4,389,418, 4,556,560, 4,569,839, 4,911,932, 4,933,330, 5,085,856, 5,208,031, 5,232,691, 5,616,331, 5,665,426, 5,730,993, 5,733,895, 5,744,146, 5,834,290, 5,863,522, 5,939,053, and 5,961,961. Some of those compositions may be sprayable (with or without a propellant). See, e.g., U.S. Pat. Nos. 4,933,330, 5,733,895, 5,834,290, 5,863,522, and 5,939,053.

Despite all the work done in this technical area, the need still exists for a safe and effective liquid skin protectant composition that is liquid, is water-repellent, substantially anhydrous, can be applied directly to the skin, quickly, easily, and without messing one's hands with the composition, and that will not run after it has been applied to the skin. Moreover, the need still exists for such a composition that can be applied to the skin without the need to use high-pressure such as that provided by propellant gas in an aerosol can. Furthermore, the need still exists for a composition meeting all those criteria that can be used for treating diaper rash.

SUMMARY OF THE INVENTION

A composition that can satisfy some or all of those needs and provides other benefits that will be apparent to one skilled in the art has now been developed. Broadly, the composition of this invention is a skin-protectant composition comprising:

(a) at least about 0.001% w of at least one active ingredient for protecting skin;

(b) at least about 0.001% w of at least one rheology modifier; and (c) carrier;

wherein the composition is liquid, is water-repellent, is substantially anhydrous, is spray-pumpable, is designed for spraying onto the skin of a baby or other human for protecting the skin, has suitable adherence to the skin, and resists running.

Another aspect of the invention concerns a skin-protectant composition comprising:

(a) at least about 0.001% w of at least one active ingredient for protecting skin;

(b) at least about 0.001% w of a rheology modifier that is an associative thickener and optionally at least about 0.001% w of at least one additional rheology modifier; and (c) carrier;

wherein the composition is liquid, is water-repellent, is substantially anhydrous, is spray-pumpable, is designed for spraying onto the skin of a baby or other human for protecting the skin, has suitable adherence to the skin, and resists running.

Another aspect of the invention concerns a skin-protectant composition comprising:

(a) at least about 0.001% w of at least one active ingredient for protecting skin;

(b) at least about 0.001% w of a rheology modifier that is an associative thickener and optionally at least about 0.001% w of at least one additional rheology modifier;

(c) at least about 0.001% w of at least one film-forming agent; and (d) carrier;

wherein the composition is liquid, is water-repellent, is substantially anhydrous, is spray-pumpable, is designed for spraying onto the skin of a baby or other human for protecting the skin, has suitable adherence to the skin, and resists running.

Another aspect of the invention concerns a skin-protectant composition comprising:

(a) at least about 0.1% w of at least one active ingredient for protecting skin;

(b) at least about 0.1% w of a rheology modifier that is an associative thickener comprising silica and optionally at least about 0.1% w of at least one additional rheology modifier;

(c) at least about 0.1% w of at least one polymeric film-forming agent; and (d) carrier;

wherein the composition is liquid, is water-repellent, is substantially anhydrous, is spray-pumpable, is designed for spraying onto the skin of a baby or other human for protecting the skin, has suitable adherence to the skin, and resists running.

Another aspect of the invention concerns a skin-protectant composition comprising:

(a) at least about 0.001% w of at least one active ingredient for protecting skin;

(b) at least about 0.001% w of at least one rheology modifier that is an associative thickener and optionally at least about 0.001% w of at least one additional rheology modifier that is a wax;

(c) at least about 0.001% w of at least one polymeric film-forming agent selected from the group consisting of silicon-containing polymers and synthetic waxes; and (d) carrier;

wherein the composition is liquid, water-repellent, is substantially anhydrous, is spray-pumpable, is designed for spraying onto the skin of a baby or other human for protecting the skin, has suitable adherence to the skin, and resists running.

Another aspect of the invention concerns a diaper rash composition comprising:

(a) at least about 0.1% w of at least one active ingredient for treating diaper rash;

(b) at least about 0.1% w of at least one rheology modifier;

(c) at least about 0.1% w of at least one film-forming agent; and (d) carrier;

wherein the composition is liquid, is water-repellent, is substantially anhydrous, is spray-pumpable, is designed for spraying onto the skin of a baby or other human for treating diaper rash, has suitable adherence to the skin, and resists running.

Another aspect of the invention concerns a diaper rash composition comprising:

(a) at least about 1% w of dimethicone;

(b) at least about 0.5% w of at least one rheology modifier selected from the group consisting of associative thickeners and waxes;

(c) at least about 0.2% w of at least one polymeric film-forming agent; and (d) carrier;

wherein the composition is liquid, is water-repellent, is substantially anhydrous, is spray-pumpable, is designed for spraying onto the skin of a baby or other human for treating diaper rash, has suitable adherence to the skin, and resists running.

Another aspect of the invention concerns a diaper rash composition comprising:

(a) at least about 1% w of dimethicone;

(b) at least about 1% w of zinc oxide;

(c) at least about 1% w of wax;

(d) at least about 1% w of an associative thickener;

(e) at least about 0.2% w of at least one polymeric film-forming agent; and (f) carrier selected from the group consisting of mineral oil and mineral oil replacements;

wherein the composition is liquid, is water-repellent, is substantially anhydrous, is spray-pumpable, is designed for spraying onto the skin of a baby or other human for treating diaper rash, has suitable adherence to the skin, and resists running.

Another aspect of the invention concerns a diaper rash composition comprising:

(a) at least about 1% w of dimethicone;

(b) at least about 1% w of mineral wax;

(c) at least about 0.5% w of silica;

(d) at least about 0.1% w of a silicon-containing polymeric film-forming agent;

(e) at least about 0.1% w of a synthetic wax polymeric film-forming agent;

(i) at least about 2% w cyclomethicone;

(g) at least about 2% w isohexadecane; and (h) at least about 50% w mineral oil;

wherein the composition is liquid, is water-repellent, is substantially anhydrous, is spray-pumpable, is designed for spraying onto the skin of a baby or other human for treating diaper rash, has suitable adherence to the skin, and resists running.

Another aspect of the invention concerns a diaper rash composition comprising:

(a) from about 0.8% w to about 1.2% w of dimethicone;

(b) from about 4% w to about 6% w of mineral wax;

(c) from about 1.8% w to about 2.8% w of silica;

(d) from about 0.8% w to about 1.2% w of a silicon-containing polymeric film-forming agent;

(e) from about 1.6% w to about 2.4% w of a synthetic wax polymeric film-forming agent;

(f) from about 7.2% w to about 10.8% w cyclomethicone;

(g) from about 5.2% w to about 7.8% w isohexadecane; and (h) from about 57% w to about 85% w mineral oil;

wherein the composition is liquid, is water-repellent, is substantially anhydrous, is spray-pumpable, is designed for spraying onto the skin of a baby or other human for treating diaper rash, has suitable adherence to the skin, and resists running.

Another aspect of the invention concerns a diaper rash composition comprising:

(a) at least about 1% w of dimethicone;

(b) at least about 1% w of zinc oxide;

(c) at least about 1% w of mineral wax;

(d) at least about 0.5% w of silica;

(e) at least about 0.1% w of a silicon-containing polymeric film-forming agent;

(f) at least about 0.1% w of a synthetic wax polymeric film-forming agent;

(g) at least about 2% w cyclomethicone;

(h) at least about 2% w isohexadecane; and (i) at least about 50% w mineral oil;

wherein the composition is liquid, is water-repellent, is substantially anhydrous, is spray-pumpable, is designed for spraying onto the skin of a baby or other human for treating diaper rash, has suitable adherence to the skin, and resists running.

Another aspect of the invention concerns a diaper rash composition comprising:

(a) from about 0.8% w to about 1.2% w of dimethicone;

(b) from about 8% w to about 12% w of zinc oxide;

(c) from about 1.8% w to about 2.7% w of mineral wax;

(d) from about 1.7% w to about 2.5% w of silica;

(e) from about 0.4% w to about 0.6% w of a silicon-containing polymeric film-forming agent;

(f) from about 1.0% w to about 1.6% w of a synthetic wax polymeric film-forming agent;

(g) from about 6.8% w to about 10.2% w cyclomethicone;

(h) from about 4.5% w to about 6.7% w isohexadecane; and (i) from about 53% w to about 80% w mineral oil;

wherein the composition is liquid, is water-repellent, is substantially anhydrous, is spray-pumpable, is designed for spraying onto the skin of a baby or other human for treating diaper rash, has suitable adherence to the skin, and resists running.

Another aspect of this invention concerns a hand-held spray pump dispenser containing and for spraying the composition of this invention.

Another aspect of this invention concerns a method of protecting human skin comprising applying the composition of this invention to human skin.

Another aspect of this invention concerns a method of treating diaper rash in a human comprising applying the composition of this invention to human skin.

The composition of this invention is safe, effective, and can be applied directly to the skin (i.e., by spraying). Spraying obviates the need to first put the composition on one's hands or on an application device and then rub it onto the skin of a baby or other human being. Such rubbing on skin already affected with, for example, diaper rash would likely cause discomfort. The composition of this invention is storage-stable, even though it can contain a significant concentration of solids, such as zinc oxide particles. The composition can be sprayed using a hand-held pump sprayer (a hand-held spray pump dispenser), that is, without the need to use a pressurized (e.g., propellant-containing) device. Hand-held spray pump dispensers are easier to use, more environmentally friendly, and their use avoids having a pressurized container used near, for example, an infant. The composition of this invention tends to resist running after it has been applied to the skin, and it has a reduced greasy feel.

Further aspects, features, and advantages of this invention will become apparent to those skilled in the art from the description of the invention herein.

DETAILED DESCRIPTION OF THE INVENTION

The composition of this invention is a liquid, water-repellent, substantially anhydrous, spray-pumpable composition that is designed for spraying onto the skin of a baby or other human being for protecting skin (e.g., for treating diaper rash). It is believed that this composition is the first skin protectant spray composition that, among other things, is liquid, is designed for direct application to the skin of a human being (including to the tender skin of a baby), is efficacious in protecting the skin to which it is applied, has suitable adherence to the skin, can contain particles (e.g., of silica), is storage-stable, water-repellent, substantially anhydrous, and spray-pumpable, and resists running. It is also believed that the diaper rash spray embodiment is the first diaper rash spray composition of its type that, among other things, is liquid, is designed for direct application to the tender skin of a baby, provides efficacious treatment of diaper rash, has suitable adherence to the skin, can contain zinc oxide particles, is storage-stable, water-repellent, substantially anhydrous, and spray-pumpable, and resists running.

By "liquid" is meant that at 20 degrees Centigrade under atmospheric pressure the substance in question has a continuous liquid phase and otherwise meets the definition of a liquid. For example, the composition of this invention is liquid before being sprayed because it has a continuous liquid phase at 20 degrees Centigrade under atmospheric pressure. Thus, for example, the presence of solid particles (e.g., of zinc oxide and/or silica) in the composition does not prevent it from being considered to be a "liquid" composition.

By "water-repellent" is meant that the composition when on the skin substantially impedes the passage of liquid water through the composition for a sufficiently long period of time. Thus, for example, in the case of a diaper rash composition of this invention, the composition is water-repellent because it impedes the passage of water for at least what is a typical period of time between diaper changes (e.g., three hours, five hours, seven hours, or in some cases even longer).

By "substantially anhydrous" is meant that the water content of the composition will be less than about 5% w by weight, typically less than about 3% w, desirably less than about 2% w, more desirably less than about 1% w, most desirably less than about 0.5% w, preferably less than about 0.3% w, more preferably less than about 0.1% w, and most preferably less than about 0.05% w. Although no water preferably is intentionally added as a separate ingredient when making the composition, it is possible that some of the ingredients used to formulate the composition may contain trace quantities of water. If any water is present in the composition of this invention, there desirably is no "free" (i.e., non-emulsified) water and, therefore, there desirably is no separate water phase. Thus, preferably, at least as may be observed using normal human vision (i.e., 20/20) without the aid of any magnifying or detection equipment, no separate aqueous layer forms when the composition of this invention stands for 24 hours at 20 degrees Centigrade in a closed container padded with inert gas.

The presence of free water in the composition tends to adversely affect the physical and other properties of the composition. More free water could create a discrete water layer and/or increase the surface tension of the composition (reducing the ability of the composition to "wet" the working parts of the spray pump dispenser and thereby be easily sprayed) and/or decrease the composition's adherence to the skin (tackiness) and/or increase its "runnyness" (i.e., the tendency of the composition to run off the skin to which it has been applied because of gravity or other force). Thus, free (i.e., non-emulsified) water in a layer of composition on skin being protected (which includes being treated) is believed to reduce the efficacy of the composition for its intended purpose of protecting skin (e.g., treating diaper rash) by reducing the sprayability of the composition, by reducing the barrier properties of the composition (including making the composition less water-repellent), and by making it easier for the composition to prematurely leave the skin being treated (e.g., to prematurely rub off or prematurely flow off under the force of gravity). If the composition were formulated to contain water, it would be necessary to add an emulsifier; however, it is a feature of this invention that the composition can be "emulsifier-free." Preferably the composition is emulsifier-free. Including an emulsifier in the composition (so that any water present is not "free") would tend to make the composition less spray-pumpable and less water-repellent, and it is a feature of this invention that the composition is spray-pumpable and water-repellent.

By "spray-pumpable" is meant that a hand-held spray pump dispenser can be used to dispense the composition, which is liquid at 20 degrees Centigrade under normal atmospheric pressure, by spraying using normal finger pressure on the portion of the spray pump assembly designed to be activated by finger pressure. By "spray" is meant a jet of finely divided liquid composition. (See, e.g., U.S. Pat. Nos. 3,159,316, 4,034,900, and 4,050,860, which show different spray pump dispensers.) The hand-held spray pump dispenser used to dispense (spray) a composition of this invention typically contains the composition at atmospheric pressure and it is only when finger pressure is applied that the spray pump mechanism temporarily pressurizes the composition to cause a portion of it to leave the dispenser as a spray. The pressure in the mechanism soon returns to atmospheric after the small portion of composition has been dispensed. Such a hand-held spray pump dispenser is considered to be a non-pressurized dispenser. In other words, a feature of this invention is that a hand-held spray pump dispenser (i.e., a non-pressurized dispenser) can be used in its normal manner to dispense the composition of this invention.

"Spray cans" or "aerosol cans," which use propellants (e.g., a FREON or other fluid having a vapor pressure at 20 degrees Centigrade significantly higher than atmospheric pressure), are well-known types of pressurized dispensers. Another type of pressurized dispenser is one having a resilient deformable bladder that has been force-filled with enough mass to cause it to expand. The memory of the resilient bladder material causes it to try to return to its original, non-deformed size and shape, which thereby pressurizes the mass inside the bladder. Another type of pressurized dispenser is a motor-driven pump (e.g., a centrifugal pump, a positive displacement pump).

The higher pressures that are provided by pressurized dispensers are not needed to dispense (spray) the composition of this invention, although in some cases they may be used. The fact that a spray-pumpable composition of this invention is also able to be dispensed using a pressurized dispenser (e.g., a dispenser containing a propellant, a dispenser containing a resilient expanded bladder, a motor-driven pump) does not mean that the composition is not spray-pumpable; however, hand-held spray pump dispensers (i.e., non-pressurized dispensers) are preferred for use in spraying the composition of this invention onto the skin to be treated. Broadly speaking, hand-held spray pump dispensers are less expensive, more economical, and more environmentally friendly than pressurized dispensers.

It is not believed that any special design for the hand-held spray pump dispenser is needed, although some adjustment of specific dimensions and/or materials of construction may be needed because of the physical and chemical properties of the particular composition to be dispensed. As will be understood by those skilled in the art, the particular design of the spray pump dispenser is not critical and any hand-held spray pump dispenser that allows appropriate dispensing of the composition of this invention, in which the composition is sufficiently storage-stable, and which itself is not adversely affected by the composition (e.g., by prolonged storage) can be used. Broadly speaking, spray pump dispensers are affected to some degree by the compositions they contain and dispense. For example, storage of the composition in the spray pump dispenser in warm weather over an extended period may cause swelling of the different parts of the spray pump dispenser to differing degrees. That in turn may adversely affect operation of the spray pump and dispensing (spraying) of the composition. Selection of a hand-held spray pump dispenser design and of suitable materials of construction are well within the skill of the art.

The terms "protecting skin," "protecting the skin," and "protecting human skin" are synonymous, have been defined above, and each include protecting and/or treating skin in connection with various indications involving the skin, including diaper rash; minor burns; cuts; scrapes; sunburn; chaffed, chapped, cracked, or windburned skin or lips; skin irritation; and oozing and/or weeping of skin caused by poison ivy, poison oak, and/or poison sumac.

The term "diaper rash" has been defined above as an inflammatory skin condition in the diaper area (perineum, buttocks, lower abdomen, and inner thighs) caused by one or more of the following factors: moisture, occlusion, chaffing, continued contact with urine or feces or both, or mechanical or chemical irritation. Thus, "diaper rash" is the well-known condition often suffered by babies and older incontinent people as a result of their wearing diapers or the like (e.g., incontinence pads). Diaper rash may also be referred to as "diaper dermatitis" or "incontinence dermatitis."

The term "treating diaper rash" has been defined above and includes treating an existing diaper rash condition or preventing a diaper rash condition or both.

A composition that is "designed for spraying onto the skin of a baby or other human" is a sprayable composition that will not harm the skin of any human being, not even the more delicate (tender) skin of a baby, will not be toxic, will not cause irritation, will not be malodorous, will not decompose to cause any harmful reactions, will not adversely affect any diaper or other substrate that may be in contact with the composition, etc. Compositions "designed for spraying onto the skin of a baby or other human" include compositions designed to be sprayed onto the skin of babies or other human beings for any indication for which a skin protectant is used.

A composition that is "designed for spraying onto the skin of a baby or other human for protecting the skin" is a composition that is "designed for spraying onto the skin of a baby or other human" and is efficacious for the purpose of protecting the skin.

A composition that is "designed for spraying onto the skin of a baby or other human for treating diaper rash" is a composition that is "designed for spraying onto the skin of a baby or other human" and is efficacious for the purpose of treating diaper rash.

A composition of this invention that has "suitable adherence to the skin" will after being applied to the skin remain adhered to the skin long enough under normal conditions of use to have an efficacious effect (for example, for treating diaper rash). A layer of composition on the skin may be thought of as a stack of parallel thin layers, each layer being at least one molecule thick. With a composition that has suitable adherence to the skin, the composition's molecular layer closest to the skin (the bottom molecular layer) will temporarily bond physically and/or chemically to the skin on a molecular level, the composition's molecular layer above the bottom molecular layer will temporarily bond physically and/or chemically to that bottom molecular layer, and so on. The bonds between the skin and the bottom molecular layer and between the successive molecular layers cannot be permanent or else it would be difficult to remove the composition from the skin.

If a composition "resists running," the composition will not, for example, under the force of gravity, easily or quickly flow from the skin to which it has been applied. The ability to "resist running" in any particular case depends not only on the physical and chemical properties of the composition itself, but also on variables such as the thickness of the layer of composition applied to the skin and the condition (e.g., oiliness, cleanliness) of the skin to which the composition was applied. The rheology modifiers, optional film-forming agents, and optional volatile carrier ingredients used in the composition help it resist running.

The ability of a composition of this invention to resist running was compared to the ability of two compositions outside the scope of invention to resist running. All of the test runs were performed at room temperature (about 20 degrees Centigrade). The preferred zinc oxide-containing composition of this invention (described in detail below) was placed in a dispenser that dispenses as a spray nominally 0.13 milliliters of composition per pump. The spray nozzle was held 2 inches (about 5.1 centimeters) above a piece of FORMICA plastic laminate lying flat on a horizontal work surface so that the centerline of the dispensing aperture in the nozzle was perpendicular to the surface of the laminate, and three "pumps" of composition were dispensed (a total of nominally 0.39 milliliters of composition). The resulting circle formed on the laminate surface by the sprayed composition was 1.5 inches (about 3.8 centimeters) in diameter. The piece of plastic laminate was rotated to a vertical position so that the plane of the circle was perpendicular to the horizontal work surface, and a line 4 inches (about 10.2 centimeters) below the bottom of the circle and parallel to the horizontal work surface was established. The preferred zinc oxide-containing composition of this invention did not run down from its 1.5-inch circle, much less traverse the 4 inches (about 10.2 centimeters), even after 2 hours.

The test was also performed on two compositions outside the scope of the invention: (1) a liquid consisting of only the mineral oil used in the preferred zinc oxide-containing composition and (2) a liquid consisting of 99% w of that mineral oil and 1% w of the dimethicone used in the preferred zinc oxide-containing composition. The 100% w mineral oil flowed down the surface of the plastic laminate and traversed the distance of 4 inches (about 10.2 centimeters) in less than a second. The liquid consisting of 99% w mineral oil and 1% w dimethicone flowed down the surface of the plastic laminate and traversed the distance of 4 inches (about 10.2 centimeters) in about 4 seconds.

As used herein, the term "resists running" means that when a composition is tested in this manner, if it is going to flow at all, it requires at least about 10 seconds to traverse (flow down) the 4 inches (in other words, it "resists running for at least about 10 seconds"), usually at least about 15 seconds to traverse the 4 inches (it "resists running for at least about 15 seconds"), typically at least about 20 seconds to traverse the 4 inches (it "resists running for at least about 20 seconds"), desirably at least about 30 seconds to traverse the 4 inches (it "resists running for at least about 30 seconds"), more desirably at least about 45 seconds to traverse the 4 inches (it "resists running for at least about 45 seconds"), most desirably at least about 1 minute to traverse the 4 inches (it "resists running for at least about 1 minute"), preferably at least about 2 minutes to traverse the 4 inches (it "resists running for at least about 2 minutes"), more preferably at least about 5 minutes to traverse the 4 inches (it "resists running for at least about 5 minutes"), most preferably at least about 10 minutes to traverse the 4 inches (it "resists running for at least about 10 minutes"), and in some cases, it requires at least about 30 minutes to traverse the 4 inches (it "resists running for at least about 30 minutes"). The most preferred compositions do not traverse the 4 inches even after an hour or more and therefore may be said to "resist running" (they "resist running for at least about 1 hour").

These tests demonstrate that the preferred zinc oxide-containing composition of this invention "resists running" and that neither of the other two compositions that were tested "resists running." The latter two compositions are outside the scope of the invention because, for example, neither contains a rheology modifier and neither resists running. The test performed with the preferred zinc oxide-containing composition also demonstrates that it has suitable adherence to the skin.

The composition of this invention has the appropriate rheology to be spray-pumpable (i.e., to have a low enough viscosity under shear) as well as to resist running after it has been applied to skin (i.e., to have a high enough viscosity when not under shear). That arises in part from the fact that one or more rheology modifiers are used to make the viscosity of the composition generally decrease as the shear on it increases (i.e., the composition may be pseudoplastic or thixotropic). Thus, as the composition that had been at rest (i.e., not flowing) in the spray pump dispenser starts to move, for example, up a tube inside the spray pump dispenser, the shear increases and the viscosity of the composition decreases. As the composition continues to move, for example, in a narrowing passage towards the small aperture in the nozzle of the spray pump dispenser, the shear continues to increase and the viscosity continues to decrease. The shear may be at a maximum, and the viscosity at a minimum, as the composition passes through the aperture in the nozzle and leaves the spray pump dispenser.

After the composition comes to rest on the skin, the force being applied to the composition is substantially less than when the composition was being forced to move inside the spray pump dispenser and through the aperture. Accordingly, the viscosity of the composition on the skin may become essentially the same as the viscosity of the composition when it was at rest inside the spray pump dispenser (and may become even higher if volatile carrier ingredients evaporate, which is what desirably happens with the compositions of this invention). This return to higher viscosity as the shear decreases plus the optional use of one or more film-forming agents help the composition resist running on the skin. In short, a "rheology modifier" is a substance otherwise suitable for incorporation into a composition of this invention that helps impart to the composition the needed transport properties and make it, for example, pseudoplastic or thixotropic.

Broadly, the composition of this invention contains at least one active ingredient for protecting skin, at least one rheology modifier, and a carrier. A preferred embodiment of this invention contains at least one active ingredient for treating diaper rash, at least one rheology modifier, and a carrier. The composition of this invention desirably also contains at least one film-forming agent. Various optional ingredients include colorants, fragrances, anti-microbials, preservatives, emollients, conditioners, adherence-promoting agents, water-resistance agents, and water-proofing agents.

The term "active ingredients for protecting skin" includes mineral oil, dimethicone, zinc oxide, allantoin, calamine, kaolin, petrolatum, white petrolatum, cod liver oil, lanolin, talc, topical starch, aluminum hydroxide gel, cocoa butter, glycerine, shark liver oil, zinc acetate, and zinc carbonate. The term "active ingredients for protecting skin" also includes other substances that are now or may in the future be efficacious for protecting skin, provided they can be successfully used alone or in combination with other active ingredients to form a composition of this invention.

The term "active ingredients for treating diaper rash" includes mineral oil, dimethicone, zinc oxide, allantoin, calamine, kaolin, petrolatum, white petrolatum, cod liver oil, lanolin, talc, and topical starch. The term "active ingredients for treating diaper rash" also includes other substances that are now or may in the future be efficacious for treating diaper rash, provided they can be successfully used alone or in combination with other active ingredients to form a composition of this invention. Of the active ingredients listed above, dimethicone is preferred and a combination of dimethicone and zinc oxide is most preferred.

The concentration of the one or more active ingredients for protecting skin should be at least about 0.001% w, usually at least about 0.01% w, desirably at least about 0.1% w, and preferably at least about 1% w. In some cases, the concentration will be at least about 5% w, at least about 10% w, or even at least about 50% w. The FDA allows a claim to be made that dimethicone is present in a composition as an active ingredient for treating diaper rash if its concentration in the composition in question is from 1% w to 30% w (and providing other FDA requirements are met). The corresponding range for zinc oxide under current FDA regulations is from 1% w to 40% w. The corresponding range for mineral oil is from 50% w to 100% w.

The limitation "at least about 0.001% w of at least one active ingredient for protecting skin" is satisfied or met (a) if any active ingredient for protecting skin is present in a concentration of at least about 0.001% w or (b) if two or more active ingredients for protecting skin are present in a total concentration of at least about 0.001% w even if none of the active ingredients for protecting skin is individually present in a concentration of at least about 0.001% w. Similarly, the limitation "at least about 0.1% w of at least one active ingredient for treating diaper rash" is satisfied or met (a) if any active ingredient for treating diaper rash is present in a concentration of at least about 0.1% w or (b) if two or more active ingredients for treating diaper rash are present in a total concentration of at least about 0.1% w even if none of the active ingredients for treating diaper rash is individually present in a concentration of at least about 0.1% w. In the same way, the limitation "at least about 0.001% w of at least one rheology modifier" is satisfied or met (a) if any rheology modifier is present in a concentration of at least about 0.001% w or (b) if two or more rheology modifiers are present in a total concentration of at least about 0.001% w even if none of the rheology modifiers is individually present in a concentration of at least about 0.001% w.

Other limitations specifying at least a certain weight percent of at least one of a certain type of ingredient should be understood that same way (making allowances, of course, for different numerical limits and types of ingredients). For example, the limitation "at least about 0.1% w of at least one film-forming agent" is satisfied or met (a) if any film-forming agent is present in a concentration of at least about 0.1% w or (b) if two or more film-forming agents are present in a total concentration of at least about 0.1% w even if none of the film-forming agents is individually present in a concentration of at least about 0.1% w.

If dimethicone is used, it will typically be present in the composition in a concentration range of about 0.01% w to about 30% w, desirably in a range of about 0.1% w to about 10% w, and preferably in a range of about 0.2% w to about 3% w. If zinc oxide is used, it will typically be present in a concentration range of about 0.01% w to about 40% w, desirably in a range of about 0.1% w to about 20% w, and preferably in a range of about 0.2% w to about 15% w. If mineral oil is used, it will typically be present in the composition in a concentration range of about 10% w to about 99% w, desirably in a range of about 50% w to about 85% w, and preferably in a range of about 55% w to about 80% w.

The dimethicone used will desirably be a crystal clear viscous liquid, free from suspended matter, and with very little odor. Any dimethicone can be used. One dimethicone found suitable has a viscosity in the range of about 333 to about 368 centistokes when measured using a Ubbelhode Size 3 viscometer at 25 degrees Centigrade and a specific gravity of about 0.96 to about 0.98 (25 degrees Centigrade/25 degrees Centigrade).

The zinc oxide used will desirably be a high purity USP (United States Pharmacopoeia) zinc oxide with a typical particle size of about 0.11 microns, a maximum particle size of about 0.14 microns, a minimum surface area (BET) of about 8 square meters per gram, a typical surface area (BET) of about 9 square meters per gram, a bulk density of about 50 pounds per cubic foot (0.80 grams per cubic centimeter), an apparent density of about 16 pounds per cubic foot (0.26 grams per cubic centimeter), and with about 99.99% of the particles passing through a 325 mesh screen. Thus, the zinc oxide used herein will typically have an average particle size of less than about 1 micron (desirably less than about 0.75 microns, more desirably less than about 0.50 microns, most desirably less than about 0.25 microns, preferably less than about 0.20 microns, and more preferably less than about 0.15 microns) and a BET surface area of at least about 5 square meters per gram. The zinc oxide particle size (and the size of any other particulates in the composition) should not be so large as to prevent the composition from being spray-pumpable.

The mineral oil is desirably light mineral oil NF (National Formulary) and is a colorless, odorless, transparent oil liquid. Its viscosity will desirably be in the range of about 7 to about 10 centistokes when measured using a Ubbelhode Size 2 viscometer at 40 degrees Centigrade, with a specific gravity of about 0.83 to about 0.84 (25 degrees Centigrade/25 degrees Centigrade).

The concentration of the one or more rheology modifiers should be at least about 0.001% w, usually at least about 0.01% w, desirably at least about 0.1% w, and preferably at least about 1% w. In some cases, the concentration will be at least about 5% w, at least about 10% w, or even at least about 20% w.

The term "rheology modifier" includes waxes and associative thickeners. The term "rheology modifier" also includes other substances that are now or may in the future be useful as rheology modifiers, provided they can be successfully used alone or in combination with other rheology modifiers to form a composition of this invention. The one or more rheology modifiers help impart the desired transport properties to the composition, that is, they help make the composition for example, pseudoplastic or thixotropic, so that it is spray-pumpable but able to resist running after it has been applied to the skin.

The wax, if used, is desirably a mineral wax. If mineral wax is used, it will typically be present in the composition in a concentration range of about 0.01% w to about 20% w, desirably in a range of about 0.1% w to about 15% w, and preferably in a range of about 0.2% w to about 6% w. The mineral wax will typically be a white to yellowish odorless waxy solid, desirably having a melting range of from about 65 degrees Centigrade to about 71 degrees Centigrade.

The associative thickener, if used, desirably comprises a silica and preferably colloidal silicon dioxide NF (National Formulary). Its particle size cannot be so large as to prevent the composition from being spray-pumpable.

Desirably the mineral wax and colloidal silicon dioxide are both used. The wax helps give the composition some body, provides internal cohesiveness (internal tack) to the layer of composition on the skin (which facilitates removal from the skin), and provides water repellency, in addition to acting as a rheology modifier. The colloidal silicon dioxide acts as a rheology modifier and if zinc oxide is present in the composition, the silicon dioxide helps to suspend the zinc oxide particles. As between these two types of rheology modifiers (waxes and associative thickeners), the associative thickeners are believed to play a larger role in giving the composition of this invention the desired transport properties to make it, for example, pseudoplastic or thixotropic.

The carrier can comprise more than one ingredient. The concentration of the carrier in the composition should be at least about 10% w, usually at least about 20% w, desirably at least about 30% w, preferably at least about 40% w, more preferably at least about 50% w, and most preferably at least about 60% w.

The term "carrier" includes mineral oil and mineral oil replacements. The term "carrier" also includes other substances that are now or may in the future be useful as carriers, provided they can be successfully used alone or in combination with other carrier ingredients to form a composition of this invention.

Mineral oil replacements include alkanes having at least 10 carbon atoms (e.g., isohexadecane), benzoate esters, aliphatic esters, noncomodogenic esters, volatile silicone compounds (e.g., cyclomethicone), and volatile silicone substitutes. Examples of benzoate esters include $C_{12}$–$C_{15}$ alkyl benzoate, isostearyl benzoate, 2-ethyl hexyl benzoate, dipropylene glycol benzoate, octyldodecyl benzoate, stearyl benzoate, and behenyl benzoate. Examples of aliphatic esters include $C_{12}$–$C_{15}$ alkyl octonoate and dioctyl maleate. Examples of noncomodogenic esters include isononyl isononanoate, isodecyl isononanoate, diisostearyl dimer dilinoleate, arachidyl propionate, and isotridecyl isononanoate. Examples of volatile silicone substitutes include isohexyl decanoate, octyl isononanoate, isononyl octanoate, and diethylene glycol dioctanoate.

If mineral oil is used, it will typically be present in the composition in a concentration range of about 10% w to about 99% w, desirably in a range of about 50% w to about 85% w, and preferably in a range of about 55% w to about 80% w.

If isohexadecane is used, it will typically be present in the composition in a concentration range of about 0.01% w to about 50% w, desirably in a range of about 0.1% w to about 15% w, and preferably in a range of about 0.2% w to about 10% w. The isohexadecane helps reduce the greasiness of the composition that might be felt if it were not present. Isohexadecane by itself tends to feel "dry" and not greasy.

If cyclomethicone is used, it will typically be present in the composition in a concentration range of about 0.01% w to about 99% w, desirably in a range of about 0.1% w to about 20% w, and preferably in a range of about 0.2% w to about 15% w. Cyclomethicone is an evaporative silicone and it helps make the composition spray-pumpable. Furthermore, after the composition is dispensed and contacts the skin, the cyclomethicone tends to evaporate, thereby helping to the composition to resist running and thereby fix the composition on the skin on which it was sprayed.

Preferably the carrier comprises a combination of mineral oil, isohexadecane, and cyclomethicone.

Desirably at least one film-forming agent is used in the composition. The concentration of the one or more film-forming agents should be at least about 0.001% w, usually at least about 0.01% w, desirably at least about 0.1% w, more desirably at least about 0.2% w, preferably at least about 1% w, and more preferably at least about 2% w. In some cases, the concentration will be at least about 5% w, at least about 10% w, or even at least about 20% w.

The term "film-forming agent" includes polymers such as silicone-containing polymers and synthetic waxes. The term "film-forming agent" also includes other substances that are now or may in the future be useful as film-forming agents, provided they can be successfully used alone or in combination with other film-forming agents to form a composition of this invention.

The silicone-containing polymers that are useful herein will typically have silicone-seeking groups and hydrophobic groups. An example of a silicone-containing polymer that may be used as a film-forming agent is a polydimethylsiloxane-polypropylene glycol ether/isopropyldiisocyanate copolymer, which is a silicone polyurethane and is described as a semi-clear faint yellow viscous liquid. Such a material is marketed under the name Polyderm PPI-SI-WI by Alzo Inc., located in Matawan, N.J., United States. If that silicone-containing polymer is used, it will typically be present in the composition in a concentration range of about 0.01% w to about 15% w, desirably in a range of about 0.1% w to about 10% w, and preferably in a range of about 0.2% w to about 3% w. This polymer functions not only as a film-forming agent but also is a conditioner and emollient, helps impart water-resistance, and helps provide adherence of the composition to the skin. This polymer also helps couple the silicone-containing components present (e.g., dimethicone and cyclomethicone) to the non-silicone-containing ingredients present (e.g., mineral oil).

An example of a synthetic wax that may be used as a film-forming agent is described as a highly branched hydrocarbon manufactured from olefins. A suitable synthetic wax may have a polydispersity of about 2.4, a number average molecular weight of about 900, and a weight average molecular weight of about 2,200. One such suitable material is marketed under the name Performa V 825 Polymer by New Phase Technologies located in Piscataway, N.J., United States. The company's "NPT Technical Bulletin 6825–1" (revision dated March 1999) describes the material as "an excellent film former and conditioner," which "provides gloss to lipsticks and improves the rheology of sunscreen formulations." If that synthetic wax is used, it will typically be present in the composition in a concentration range of about 0.01% w to about 30% w, desirably in a range of about 0.1% w to about 10% w, and preferably in a range of about 0.2% w to about 6% w. This synthetic wax functions not only as a film-forming agent but also helps impart water-resistance.

Many different optional ingredients may be included in the composition, including colorants, fragrances, anti-microbials, preservatives, emollients, conditioners, adherence-promoting agents, water-resistance agents, and water-proofing agents. For example, an aloe barbadensis product may be included as may vitamins such as vitamin E. An aloe product, if used in the composition, will typically be present in the composition in a concentration range of about 0.01% w to about 15% w, desirably in a range of about 0.1% w to about 10% w, and preferably in a range of about 0.2% w to about 6% w. Vitamin E, if used in the composition, will typically be present in the composition in a concentration range of about 0.01% w to about 5% w, desirably in a range of about 0.1% w to about 3% w, and preferably in a range of about 0.2% w to about 1% w, and may be added in its acetate ester form.

A preferred composition without zinc oxide and a preferred composition with zinc oxide are shown below (numerical values are weight percentages).

| Ingredient | Preferred Composition Without Zinc Oxide | Preferred Composition With Zinc Oxide |
|---|---|---|
| Mineral Oil | 70.95 | 66.50 |
| Polyderm PPI-SI-WI | 1.00 | 0.50 |
| Dimethicone | 1.00 | 1.00 |
| Mineral Wax | 5.00 | 2.25 |
| Performa V 825 Polymer | 2.00 | 1.30 |
| Colloidal Silicon Dioxide | 2.30 | 2.10 |
| Cyclomethicone | 9.00 | 8.50 |
| Isohexadecane | 6.50 | 5.60 |
| Aloe Barbadensis Extract | 2.00 | 2.00 |
| Vitamin E Acetate | 0.25 | 0.25 |
| Zinc Oxide | 0.00 | 10.00 |
| Total | 100.00 | 100.00 |

A typical process for manufacturing the preferred composition with zinc oxide is as follows. The first five ingredients (mineral oil, Polyderm PPI-SI-WI, dimethicone, mineral wax, and Performa V 825 Polymer) are placed in a suitable stainless steel container and heated to about 80 degrees Centigrade while mixing at slow speed. After the mineral wax melts, heating is halted and the zinc oxide is added while mixing at about 500 RPM (revolutions per minute) for at least 10 minutes. When the batch cools to about 50 degrees Centigrade (while still mixing), the colloidal silicon dioxide is added and the mixing speed is increased to about 2,000 RPM and held at that speed for at least 20 minutes. The remaining ingredients (cyclomethicone, isohexadecane, aloe barbadensis extract, and vitamin E acetate) are then added and mixing is continued for about 15 minutes. At the end of this time, the material is milled to further homogenize it and the manufacture is then complete. To make the preferred composition that does not contain the zinc oxide, the process is essentially the same, the major difference being that the step in which the zinc oxide is added is omitted. The processes for making other compositions of the invention are well within the skill of the art.

When the composition contains solid suspended particles (e.g., the zinc oxide and/or colloidal silica), it might be seem to be more appropriate to refer to the composition as a dispersion or suspension rather than as a liquid. However, even though solid particles may be present, the composition of this invention will still be referred to as a "liquid" because (a) the continuous phase of the composition is liquid and typically will account for the majority of the composition (and preferably about 90% w of it) and (b) the user will likely perceive such a composition as being "liquid."

For a variety of reasons, such a dispersion or suspension is desirably storage-stable, that is, the particles desirably do not settle out, even after prolonged standing. When zinc oxide particles are present, the silica (e.g., colloidal silicon dioxide) helps prevent their settling. If particles do settle out, they should be readily and easily redispersable and resuspendable, preferably merely by shaking the composition a few times.

As will be apparent, a single ingredient can perform more than a single function in a composition of this invention. Thus, it should be understood in applying the claims to a given composition that because an ingredient of the composition may perform more than one function, that one ingredient may thereby satisfy (or meet) more than one limitation of a claim. For example, mineral oil, which can act as an active ingredient, is also a preferred carrier. If mineral oil is present in a composition in at least the minimum concentration for an active ingredient for protecting skin specified by the limitation of a given claim, then the mineral oil of that composition meets that claim limitation. If the mineral oil is also present in that composition in at least the minimum concentration specified for the carrier by another limitation of the same claim, then the mineral oil of that composition also meets that limitation of the claim. Thus, the same ingredient and amount of ingredient can satisfy more than a single limitation of a claim. (If no numerical minimum is specified in a claim limitation that requires the presence of an ingredient, for example, a limitation that just requires "carrier," that limitation is satisfied (or met) if at least some of the ingredient is present.)

Variations and modifications will be apparent to those skilled in the art and the claims are intended to cover all modifications and variations that fall within the true spirit and scope of the invention.

We claim:

1. A diaper rash composition comprising: (a) at least about 1% w of dimethicone; (b) at least about 1% w of mineral wax; (c) at least about 0.5% w of silica; (d) at least about 0.1% w of a silicon-containing polymeric film-forming agent; (e) at least about 0.1% w of a synthetic wax polymeric film-forming agent; (f) at least about 2% w cyclomethicone; (g) at least about 2% w isohexadecane; and (h) at least about 50% w mineral oil; wherein the composition is liquid, is water-repellent, is substantially anhydrous, is spray-pumpable, is designed for spraying onto the skin of a baby or other human for treating diaper rash, has suitable adherence to the skin, and resists running.

2. A diaper rash composition comprising: (a) from about 0.8% w to about 1.2% w of dimethicone; (b) from about 4% w to about 6% w of mineral wax; (c) from about 1.8% w to about 2.8% w of silica; (d) from about 0.8% w to about 1.2% w of a silicon-containing polymeric film-forming agent; (e) from about 1.6% w to about 2.4% w of a synthetic wax polymeric film-forming agent; (f) from about 7.2% w to about 10.8% w cyclomethicone; (g) from about 5.2% w to about 7.8% w isohexadecane; and (h) from about 57% w to about 85% w mineral oil; wherein the composition is liquid, is water-repellent, is substantially anhydrous, is spray-pumpable, is designed for spraying onto the skin of a baby or other human for treating diaper rash, has suitable adherence to the skin, and resists running.

3. A diaper rash composition comprising: (a) at least about 1% w of dimethicone; (b) at least about 1% w of zinc oxide; (c) at least about 1% w of mineral wax; (d) at least about 0.5% w of silica; (e) at least about 0.1% w of a silicon-containing polymeric film-forming agent; (f) at least about 0.1% w of a synthetic wax polymeric film-forming agent; (g) at least about 2% w cyclomethicone; (h) at least about 2% w isohexadecane; and (i) at least about 50% w mineral oil;

wherein the composition is liquid, is water-repellent, is substantially anhydrous, is spray-pumpable, is designed for spraying onto the skin of a baby or other human for treating diaper rash, has suitable adherence to the skin, and resists running.

4. A diaper rash composition comprising: (a) from about 0.8% w to about 1.2% w of dimethicone; (b) from about 8% w to about 12% w of zinc oxide; (c) from about 1.8% w to about 2.7% w of mineral wax; (d) from about 1.7% w to about 2.5% w of silica; (e) from about 0.4% w to about 0.6% w of a silicon-containing polymeric film-forming agent; (f) from about 1.0% w to about 1.6% w of a synthetic wax polymeric film-forming agent; (g) from about 6.8% w to about 10.2% w cyclomethicone; (h) from about 4.5% w to about 6.7% w isohexadecane; and (i) from about 53% w to about 80% w mineral oil; wherein the composition is liquid, is water-repellent, is substantially anhydrous, is spray-pumpable, is designed for spraying onto the skin of a baby or other human for treating diaper rash, has suitable adherence to the skin, and resists running.

5. A hand-held spray pump dispenser containing the composition of any one of claims 1 to 4 for spraying the composition.

6. A method of protecting human skin comprising applying the composition of any one of claims 1 to 4 to human skin.

7. A method of treating diaper rash in a human comprising applying the composition of any one of claims 1 to 4 to human skin.

* * * * *